US008435509B2

(12) United States Patent
Brink et al.

(10) Patent No.: US 8,435,509 B2
(45) Date of Patent: *May 7, 2013

(54) CREATION OF A BIOLOGICAL ATRIOVENTRICULAR BYPASS TO COMPENSATE FOR ATRIOVENTRICULAR BLOCK

(75) Inventors: Peter R Brink, Setauket, NY (US); Ira S Cohen, Stony Brook, NY (US); Michael R Rosen, New York, NY (US); Richard B Robinson, Cresskill, NJ (US); Peter Danilo, Hopewell, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/109,804

(22) Filed: May 17, 2011

(65) Prior Publication Data

US 2011/0223144 A1    Sep. 15, 2011

Related U.S. Application Data

(62) Division of application No. 10/584,303, filed as application No. PCT/US2004/042953 on Dec. 22, 2004, now Pat. No. 7,968,126.

(60) Provisional application No. 60/532,363, filed on Dec. 24, 2003.

(51) Int. Cl.
*C12N 5/07* (2010.01)
*C12N 5/071* (2010.01)
*C12N 5/10* (2006.01)
*A61P 9/00* (2006.01)

(52) U.S. Cl.
USPC ........ 424/93.21; 424/93.7; 435/6.1; 435/325; 435/370

(58) Field of Classification Search .................. None
See application file for complete search history.

(56) References Cited

U.S. PATENT DOCUMENTS 7,034,008 B2 * 4/2006 Donahue et al. ............ 514/44 R
2004/0137621 A1 * 7/2004 Rosen et al. ................. 435/455

OTHER PUBLICATIONS

O'Grady et al, 2005, The International Journal of Biochemistry and Cell Biology, 37: 1578-1594.*
Kaupp et al., 2001, Annual Review of Physiology, 63: 235-257.*
Kaye et al., 1990, Proc. Natl. Acad. Sci. USA, 87: 6922-6926.*
Skolnick et al., 2000, Trends in Biotech., 18: 34-39.*
Tomasinsig et al., 2005, Current Protein and Peptide Science, 6: 23-34.*

* cited by examiner

*Primary Examiner* — Julie Ha
(74) *Attorney, Agent, or Firm* — Evans & Molinelli PLLC; Judith A. Evans

(57) ABSTRACT

The invention provides a method of creating an atrioventricular bypass tract for a heart comprising growing mesenchymal stem cells into a strip with two ends, and attaching one end of the strip onto the atrium of the heart, and attaching the other end of the strip to the ventricle of the heart. By this attachment, a tract is created that connects the atrium to the ventricle to provide a path for electrical signals generated by the sinus node to propagate across the tract and excite the ventricle.

13 Claims, 4 Drawing Sheets

CREATION OF A BIOLOGICAL ATRIOVENTRICULAR BYPASS TO COMPENSATE FOR ATRIOVENTRICULAR BLOCK

This application claims the benefit of, and priority from, U.S. Provisional Application No. 60/532,363, filed Dec. 24, 2003.

The invention disclosed herein was made at least in part with funding by the U.S. Government, specifically the USPH5, and NHLBI under grant number HL-28958. Therefore, the U.S. Government has certain rights in this invention.

BACKGROUND OF THE INVENTION

Throughout this application, various publications are referenced to as footnotes or within parentheses. Disclosures of these publications in their entireties are hereby incorporated by reference into this application to more fully describe the state of the art to which this invention pertains. Full bibliographic citations for these references may be found at the end of this application, preceding the claims.

One of the major indications for electronic pacemaker therapy is high degree heart block, such that a normally functioning sinus node impulse cannot propagate to the ventricle. The result is ventricular arrest and/or fibrillation, and death.

Acute myocardial infarction (MI) afflicts millions of people each year inducing significant mortality and, in a large number of survivors, marked reductions in myocyte number and in cardiac pump function. Adult cardiac myocytes divide only rarely, and the usual response to myocyte cell loss is hypertrophy that often progresses to congestive heart failure, a disease with a significant annual mortality. There have been recent reports of the delivery of mesenchymal stem cells (MSCs a multipotent cell population of blood lineage) to the hearts of post-Mi patients resulting in improved mechanical performance[1,2]. The presumption in these and other animal studies[3], is that the MSCs integrate into the cardiac syncytium and then differentiate into new heart cells restoring mechanical function.

SUMMARY OF THE INVENTION

The present invention uses biological means for cell therapy to build a bypass tract in the heart that will take over the function of a diseased atrioventricular node. Adult human mesenchymal stem cells (hMSCs) may be prepared in one of four ways (see below) and grown in culture on a non-bioreactive material. Once growth is complete the material has one end sutured to the atrium, and the other to the ventricle. Electrical signals generated by the sinus node to activate the atria will propagate across the artificially constructed tract to excite the ventricle as well. In this way the normal sequence of atrioventricular activation will be maintained.

Four methods that may be used for preparing the hMSCs are:

1: In culture without incorporation of additional molecular determinants of conduction. Here the cells' own characteristic to generate gap junctions that communicate electrical signals are used as a means to propagate an electronic wave from atrium to ventricle.
2: In culture following electroporation to add the gene for connexins 43, 40 and/or 45, the culture's electrotonic propagation of atrial signals to the ventricle.
3: In culture following electroporation to add the alpha and the accessory subunits of the L-type calcium channel, thereby increasing the likelihood of not just electrotonic propagation of a wavefront, but its active propagation by an action potential.
4: A combination of 2 and 3.

The preparation of a bypass in this fashion not only will facilitate propagation from atrium to ventricle, but will provide sufficient delay from atrial to ventricular contraction to maximize ventricular filling and emptying. The goal is to mimic the normal activation and contractile sequence of the heart. Moreover, this approach, when used with gene therapy and stem cell technology to improve atrial impulse initiation in the setting of sinus node disease offers a completely physiologic system rather than its electronic replacement.

According to the invention, a method of creating an atrioventricular bypass tract for a heart is provided, comprising growing mesenchymal stem cells into a strip with two ends, attaching one end of the strip onto the atrium of the heart, and attaching the other end of the strip to the ventricle of the heart, to create a tract connecting the atrium to the ventricle to provide a path for electrical signals generated by the sinus node to propagate across the tract and excite the ventricle.

C,D Single channel recordings from pairs of hMSCs. Pulse protocol ($V_1$ and $V_2$) and associated multichannel currents (Iz) recorded from a cell pair during maintained $V_j$ of ±80 mV. The discrete current steps indicate the opening and closing of single channels. Dashed line: zero current level. The all points current histograms on the right-hand side revealed a conductance of ~50 pS. Glass coverslips with adherent cells were transferred to an experimental chamber perfused at room temperature (~22° C.) with bath solution containing (mM): NaCl, 150; KCl, 10; $CaCl_2$, 2; HEPES, 5 (pH 7.4); glucose, 5. The patch pipettes were filled with solution containing (mM): $K^+$ aspartate$^-$, 120; NaCl, 10; MgATP, 3; HEPES, 5 (pH 7.2); EGTA, 10 (pCa~8); filtered through 0.22 μm pores. When filled, the resistance of the pipettes measured 1-2 MΩ. Experiments were carried out on cell pairs using a double voltage-clamp. This method permitted to control the membrane potential ($V_m$) and measure the associated junctional currents (Ij).

Figure 3:
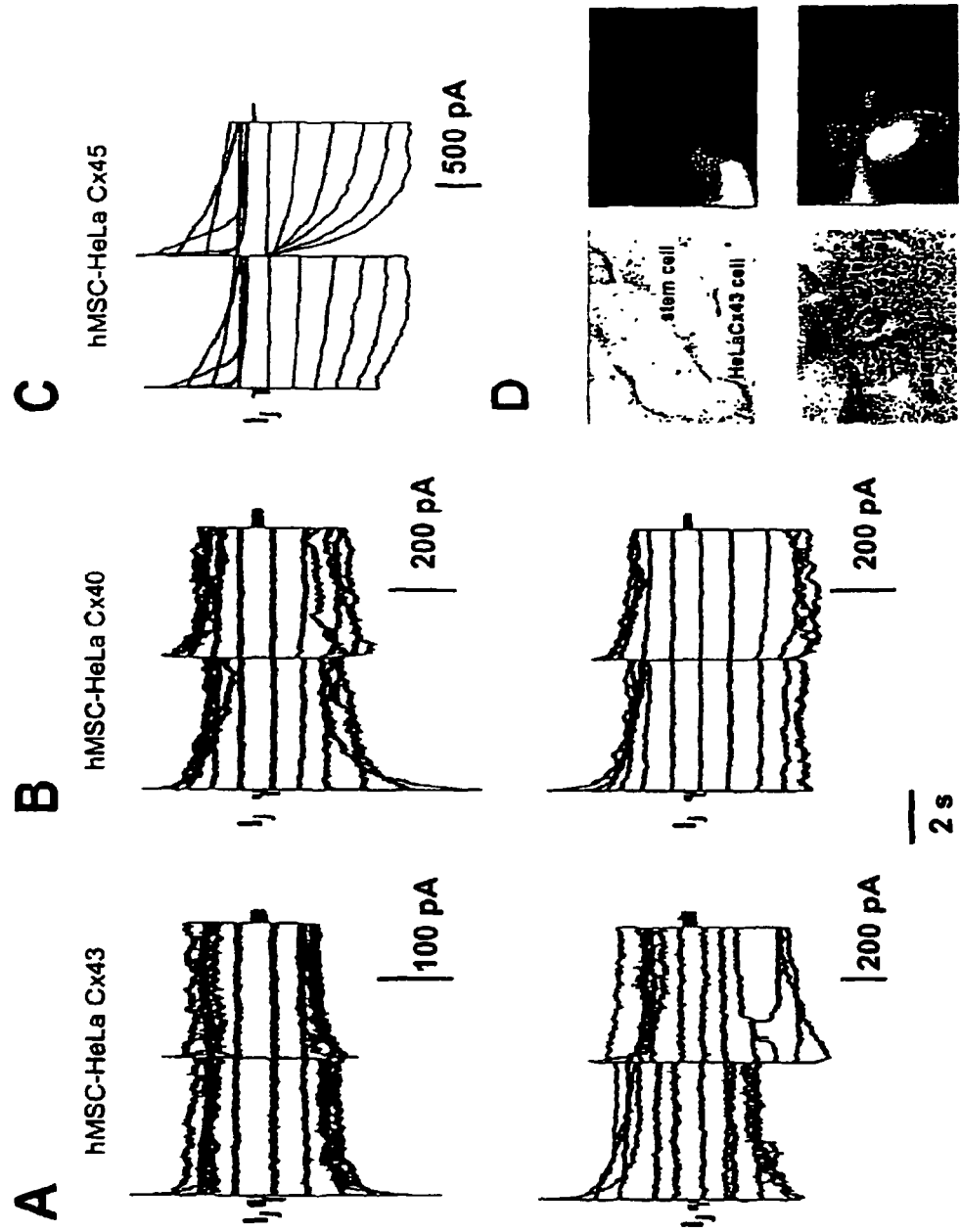

FIG. 3. Macroscopic properties of junctions in cell pairs between a hMSC and HeLa cell expressing only Cx40, Cx43 or Cx45. In all cases hMSC to Hela cell coupling was tested 6 to 12 after hours initiating co-culture.

A, Ij elicited in response to a series of voltage steps ($V_j$) in hMSC-HeLaCx43 pairs.

Top: symmetrical current deactivation; bottom: asymmetrical current voltage dependence.

B, Macroscopic Ij recordings from hMSC-HeLaCx40 pairs exhibit symmetrical (top panel) and asymmetrical (bottom panel) voltage dependent deactivation.

C, Asymmetric Ij from hMSC-HeLaCx43 pair exhibits voltage dependent gating when Cx45 side is relative negative. Ij recorded from hMSC.

D, Cell-to-cell. LY spread in cell pairs: from a HeLa Cx43 to an hMSC (top panel) and from an hMSC to a HeLa Cx43 to (bottom panel). In both cases a pipette containing 2 mM LY was attached to the left-handed cell in the whole-cell configuration.

Epifluorescent micrographs taken at 12 min after dye injection show LY spread to the adjacent (right-handed) cell. The simultaneously measured junctional conductance[6] revealed $g_j$ of ~16 nS and ~18 nS of the pairs, respectively. Cell Tracker green was used to distinguish hMSCs from HeLa cells or vice versa in all experiments[8].

Figure 4:
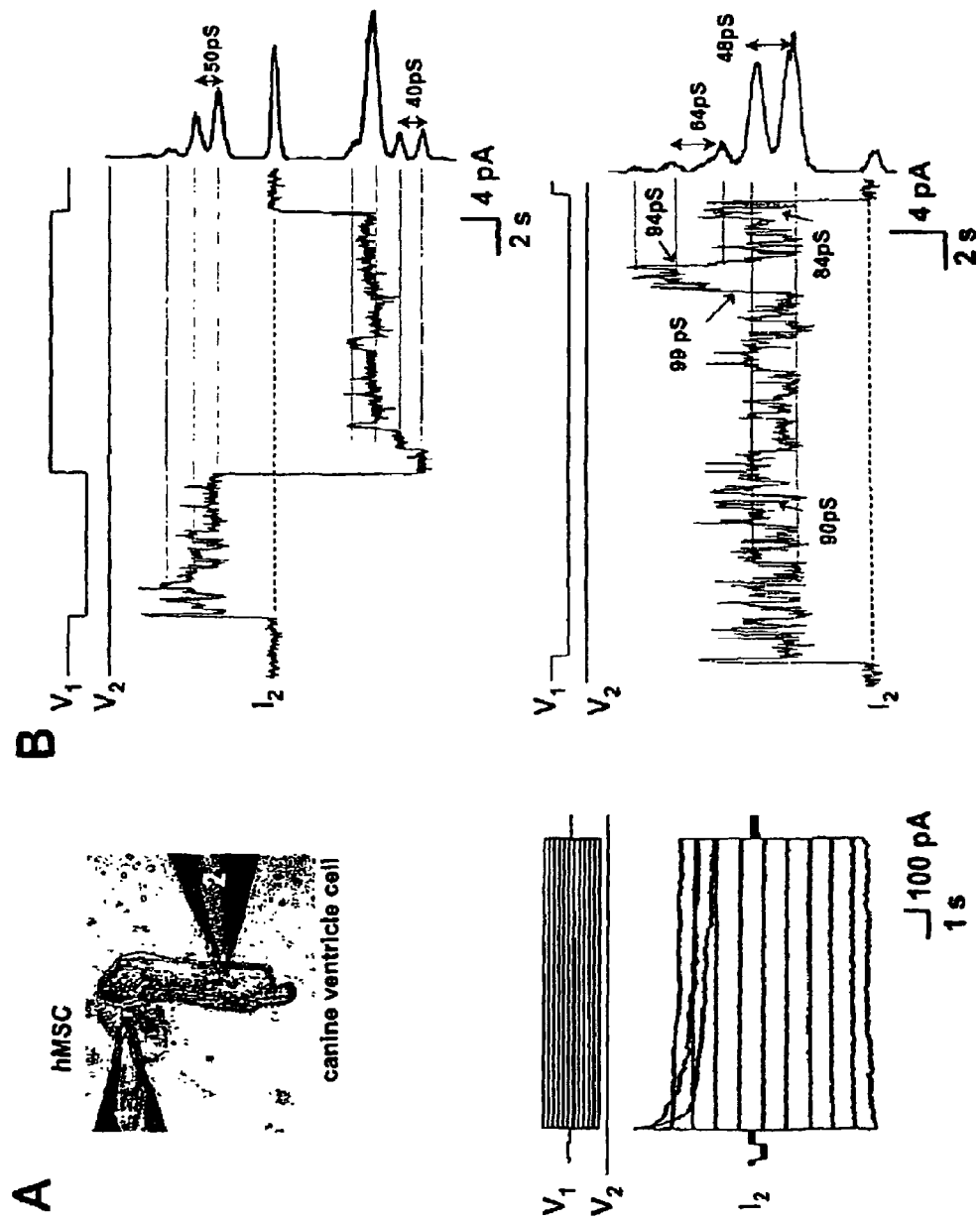

FIG. 4. Macroscopic and single channel properties of gap junctions between hMSC-canine ventricle cell pairs. Myocytes were plated between 12 and 72 hours and co-cultured with hMSCs for 6 to 12 hours before measuring coupling. A, Top panel: Phase-contrast micrograph of a hMSC-canine ventricle pair. Bottom pane: Monopolar pulse protocol ($V_1$ and $V_2$) and associated macroscopic junctional currents (Iz) exhibiting asymmetrical voltage dependence. B, Top panel: Multichannel current elicited by symmetrical biphasic 60 mV pulse. Dashed line, zero current level; dotted lines, represent discrete current steps indicative of opening and closing of channels. The current histograms yielded a conductance of ~40-50 pS. Bottom panel: Multichannel recording during maintained $V_j$ of 60 mV. The current histograms revealed several conductances of 48 to 64 pS with several events with conductance of 84 pS to with 99 pS (arrows) which resemble operation of Cx43, heterotypic Cx40-Cx43 and/or homotypic Cx40 channels.

DESCRIPTION OF THE INVENTION

According to the invention, a method of creating an atrioventricular bypass tract for a heart is provided, comprising growing mesenchymal stem cells into a strip with two ends, attaching one end of the strip onto the atrium of the heart, and attaching the other end of the strip to the ventricle of the heart, to create a tract connecting the atrium to the ventricle to provide a path for electrical signals generated by the sinus node to propagate across the tract and excite the ventricle.

The steps of attaching may be performed by suturing. The stem cells may be adult human mesenchymal stem cells. The step of growing may comprise growing the stem cells in culture on a non-bioreactive material. The step of growing may be performed in an environment substantially free of any additional molecular determinants of conduction.

The method may further comprise a step of adding a gene to the mesenchymal stem cells by electroporation. The gene may encode for a connexin, such as connexin 40, connexin 43, and/or connexin 45. The step of adding a gene by electroporation may include adding alpha and accessory subunits of L-type calcium. The step of adding a gene by electroporation may include adding the gene for connexions and adding alpha and accessory subunits of L-type calcium channel.

MSCs express connexins that are the building block proteins of gap junctions and can form functional gap junctions with one another, with cell lines expressing cardiac connexins, and with adult cardiac myocytes. Further, the connexins expressed suggest that hMSCs should readily integrate into electrical syncytia of many tissues promoting repair or serving as the substrate for a therapeutic delivery system.

Figure 1:
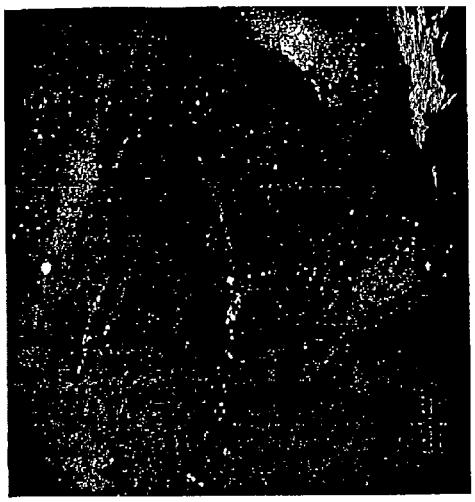
FIG. 1. Identification of connexins in gap junctions of hMSCs. Immunostaining of Cx43 (A), Cx40 (B) and Cx45 (C). D, Immunoblot analysis of Cx43 in canine ventricle myocytes and hMSCs. Whole cell lysates (120 jig) from ventricle cells or hMSCs were resolved by SDS, transferred to membranes, and blotted with Cx43 antibodies. Migration of molecular weight markers is indicated to the right to the blot.
Figure 1:
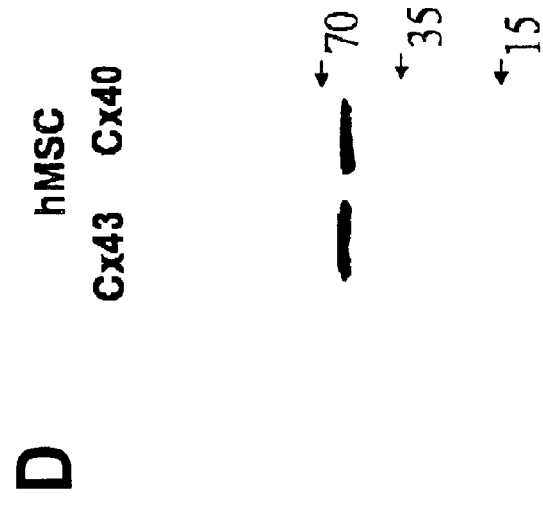
Figure 1:
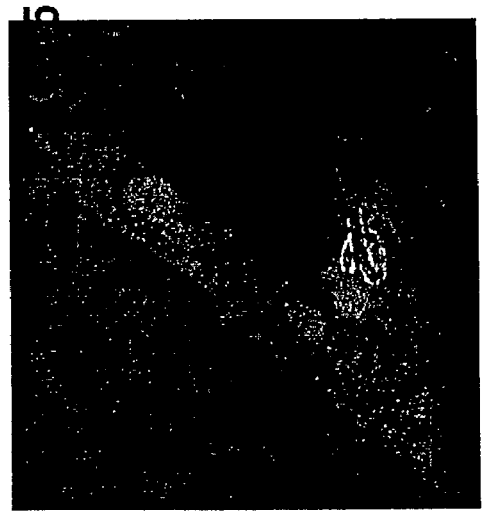

Human mesenchymal stem cells POIETICS™ hMSCs—Mesenchymal stem cells, Human Bone Marrow) were purchased from Clonetics/BioWhittaker (Walkersville, Md.) and cultured in MCS growing media and used from passages 2-4. Typical punctate staining for Cx43 and Cx40 was seen along regions of intimate cell to cell contact of the MSCs grown in culture as monolayers (FIG. 1A, B). Cx45 staining was also detected but unlike that of Cx43 or Cx40 was not typical of connexin distribution in cells. Rather it was characterized by fine granular cytoplasmic and reticular-like staining with no readily observed membrane associated plaques (FIG. 1C). This does not exclude the possibility that Cx45 channels exist but does imply that their number relative to Cx43 and Cx40 homotypic, heterotypic and heteromeric channels is low. FIG. 1D illustrates Western blot analysis[4] for canine ventricle myocytes and hMSCs with a Cx43 polyclonal antibody which adds further proof of Cx43 presence in hMSCs.

Figure 2:
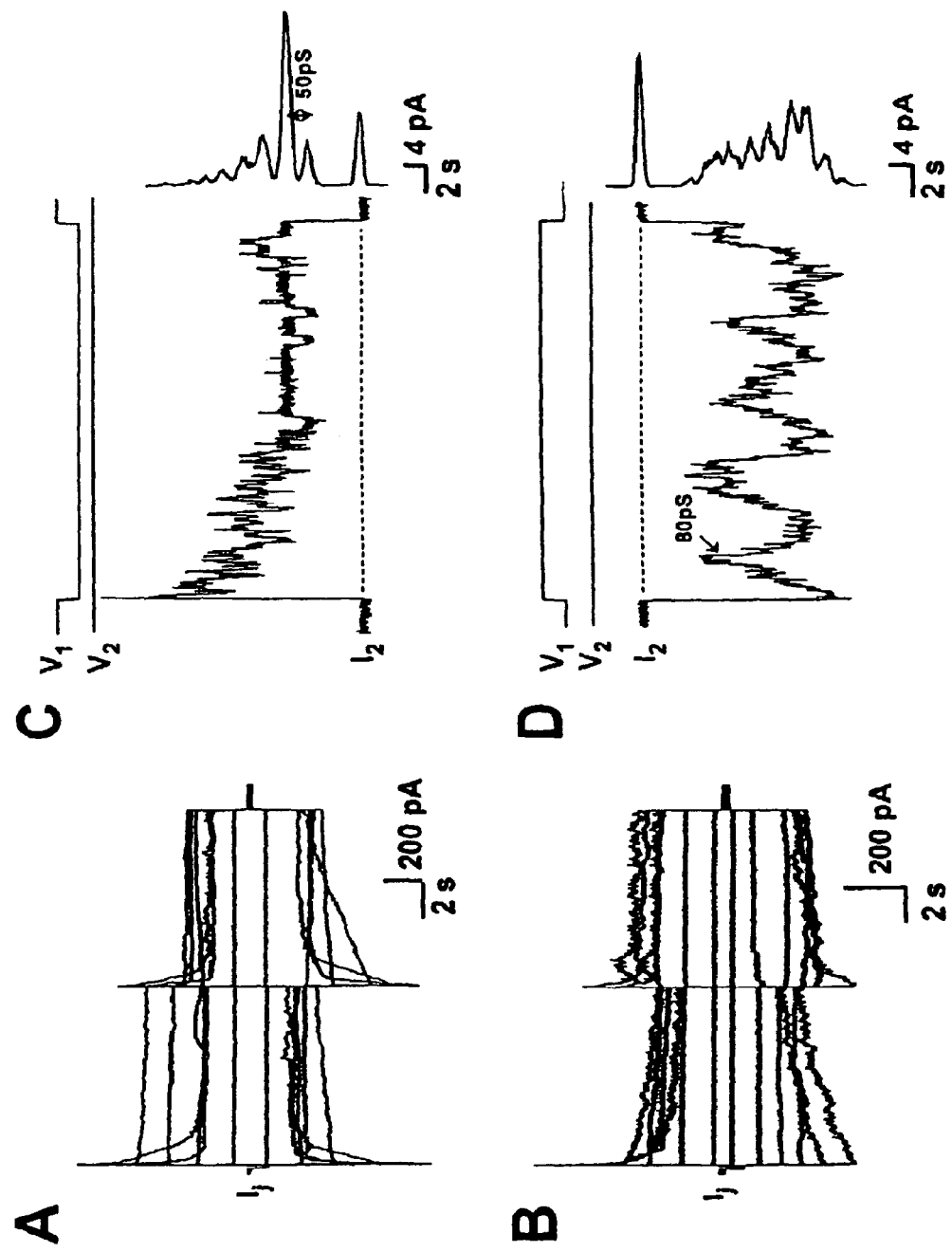
FIG. 2. Macroscopic and single channel properties of gap junctions between hMSC pairs. Gap junction currents (Ij) elicited from hMSCs using symmetrical bipolar pulse protocol showed two types of voltage dependent current deactivation: (A)-symmetrical, (B): asymmetrical.

Gap junctional coupling among hMSCs is demonstrated in FIG. 2. Junctional currents recorded between hMSC pairs show quasi-symmetrical (FIG. 2A) and asymmetrical (FIG. 2B) voltage dependency arising in response to symmetric transjunctional voltage steps of equal amplitude but opposite sign. These behaviors are typically observed in cells which co-express Cx43 and Cx40[4].

FIGS. 2C and 2D illustrate typical multichannel recordings from a hMSC pair. Using 120 mM K aspartate as a pipette solution channels were observed with unitary conductances of 28-80 pS range. Operation of channels with ~50 pS conductance (see FIG. 2 C) is consistent with previously published values[5,6] for Cx43 homotypic channels. This does not preclude the presence of other channel types, it merely suggests that Cx43 forms functional channels in hMSCs.

To further define the nature of the coupling hMSCs were co-cultured with human HeLa cells stably transfected with Cx43, Cx40, and Cx45[7] and it was found that hMSCs were able to couple to all these transfectants. FIG. 3A shows an example of junctional currents recorded between an hMSC and HeLaCx43 cell pairs that manifested symmetrically and asymmetrically voltage dependent currents. The quasi-symmetric record suggests that the dominant functional channel is homotypic Cx43 while the asymmetric record suggests the activity of another connexin in the hMSC (presumably Cx40 as shown by immunohistochemistry, see FIG. 1) that could be either a heterotypic or heteromeric form or both. These records are similar to those published for transfected cells: heterotypic and mixed (heteromeric) forms of Cx40 and Cx43[4,8]. Co-culture of hMSCs with HeLa cells transfected with Cx40 (FIG. 3B) also revealed symmetric and asymmetric voltage dependent junctional currents consistent with the co-expression of Cx43 and Cx40 in the hMSCs similar to the data for Cx43 HeLa-hMSC pairs. HeLa cells transfected with Cx45 coupled to hMSCs always produced asymmetric junctional currents with pronounced voltage gating when Cx45 (HeLa) side was negative (FIG. 3C). This is consistent with the dominant channel forms in the hMSC being Cx43 and Cx40 as both produce asymmetric currents when they form heterotypic channels with Cx45[4,8]. This does not exclude Cx45 as a functioning channel in hMSCs but it does indicate that Cx45 is a minor contributor to cell to cell coupling in hMSCs.

The lack of visualized plaques in the immunostaining for Cx45 (FIG. 1) further supports this interpretation.

FIG. 3D shows Lucifer Yellow transfer from HeLaCx43 cell to an hMSC cell (top panel) and transfer from an hMSC to a HeLaCx43 (bottom panel). The junctional conductance of the cell pairs was simultaneously measured by methods described earlier[6] and revealed conductances of ~16 nS and ~18 nS, respectively. The transfer of Lucifer Yellow was similar to that previously reported for homotypic Cx43 or co-expressed Cx43 and Cx40 in HeLa cells[6]. Cell Tracker green (Molecular Probes) was always used in one of the two populations of cells to allow heterologous pairs to be identified[8].

hMSCs were also co-cultured with adult canine ventricular myocytes. As shown in FIG. 4 the hMSCs couple electrically with cardiac myocytes. Both macroscopic (FIG. 4A) and multichannel (FIG. 4B) records were obtained. Junctional currents in FIG. 4A are asymmetric while those in FIG. 4B show unitary events of the size range typically resulting from the operation of homotypic Cx43 or heterotypic Cx43-Cx40 or homotypic Cx40 channels[4,8]. Heteromeric forms are also possible whose conductances are the same or similar to homotypic or heterotypic forms.

In studies of cell pairs were demonstrated effective coupling of hMSC to other hMSC (13.8±2.4 nS, n=14), to HeLa Cx43 (7.9±2.1 ns, n=7), to HeLa Cx40 (4.6±2.6 nS, n=5), to HeLa Cx45 (11±2.6 nS, n=5) and to ventricular myocytes (1.5±1.3 nS, n=4). Results show that hMSCs couple to one another via Cx43 and Cx40. In addition, they form functional gap junction channels with cells transfected with Cx43, Cx40 or Cx45 as well as canine ventricular cardiomyocytes. These data support the possibility of using MSCs as a therapeutic substrate for repair of cardiac tissue. Other syncytia such as vascular smooth muscle or endothelial cells should also be able to couple to the hMSCs because of the ubiquity of Cx43 and Cx40[9,10]. Thus they may also be amenable to hMSCs based therapeutics, as follows: hMSCs can be transfected to express ion channels which then can influence the surrounding synctial tissue.

Alternatively, the hMSCs can be transfected to express genes that produce small therapeutic molecules capable of permeating gap junctions and influencing recipient cells. Further, for short term therapy, the small molecules can be directly loaded into hMSCs for delivery to recipient cells. The success of such an approach is dependent on gap junction channels as the final conduit for delivery of the therapeutic agent to the recipient cells. The feasibility of one such approach was demonstrated by transfecting hMSCs with mHCN2, a gene encoding the cardiac pacemaker channel, and delivering them to the canine heart where they generate a spontaneous rhythm.

REFERENCES

1. Strauer, B. E. et al Repair of infarcted myocardium by autologous intracoronary mononuclear bone marrow cell transplantation in humans. *Circulation* 106, 1913-1918 (2002).
2. Perin, E. C., Geng, Y. J. & Willerson, J. T. Adult stem cell therapy in perspective. *Circulation* 107, 935-938 (2003).
3. Orlic, D. et al. Bone marrow cells regenerate infarcted myocardium. *Nature* 410, 701-705 (2001).
4. Valiunas, V., Gemel, J., Brink, P. R. & Beyer, E. C. Gap junction channels formed by coexpressed connexin40 and connexin43. *Am. J. Physiol. Heart Circ. Physiol.* 2001. October; 281. (4.):H1675. -89. 281, H1675-H1689 (2001).
5. Valiunas, V., Bukauskas, F. F. & Weingart, R. Conductances and selective permeability of connexin43 gap junction channels examined in neonatal rat heart cells. *Circ. Res.* 80, 708-719 (1997).
6. Valiunas, V., Beyer, E. C. & Brink, P. R. Cardiac gap junction channels show quantitative differences in selectivity. *Circ. Res.* 91, 104-111 (2002).
7. Elfgang, C. et al. Specific permeability and selective formation of gap junction channels in connexin-transfected HeLa cells. *J. Cell Biol.* 129, 805-817 (1995).
8. Valiunas. V., Weingart. R. & Brink. P. R. Formation of heterotypic gap junction channels by connexins 40 and 43. *Circ. Res.* 2000. Feb. 4; 86. (2.):E42.-9.86,E42-E49 (2000).
9. Wang. H. Z. et al. Intercellular communication in cultured human vascular smooth muscle cells. *Am. J. Physiol Cell Physiol* 281, C75-C88 (2001).
10. Beyer. E. C. Gap junctions. *Int. Rev. Cytol.* 137C, 1-37 1993).

What is claimed is:

1. An atrioventricular bypass tract for a heart that provides a path for electrical signals generated by the sinus node to propagate across the tract and excite the ventricle, made according to a method comprising
   growing mesenchymal stem cells in vitro into a strip with two ends;
   attaching one end of the strip onto the atrium of the heart; and
   attaching the other end of the strip to the ventricle of the heart, to create a tract connecting the atrium to the ventricle to provide a path for electrical signals generated by the sinus node to propagate across the tract and excite the ventricle.

2. The bypass tract of claim 1, wherein the stem cells are adult human mesenchymal stem cells.

3. The bypass tract of claim 1, wherein the stem cells are grown in culture on a non-bioactive material.

4. The bypass tract of claim 1, wherein the stem cells are grown in an environment substantially free of additional molecular determinants of conduction.

5. The bypass tract of claim 1, further comprising a step of adding a nucleic acid encoding a protein or peptide or biologically active fragment thereof to the mesenchymal stem cells.

6. The bypass tract of claim 5, wherein the nucleic acid encodes a connexin.

7. The bypass tract of claim 6, wherein the connexin is connexin 40.

8. The bypass tract of claim 6, wherein the connexin is connexin 43.

9. The bypass tract of claim 6, wherein the connexin is connexin 45.

10. The bypass tract of claim 5, wherein the step of adding nucleic acids includes adding nucleic acids that encode alpha and accessory subunits of a L-type calcium channel.

11. The bypass tract of claim 5, further comprising adding nucleic acids that encode alpha and accessory subunits of a L-type calcium channel.

12. The bypass tract of claim 5, wherein the nucleic acid encodes a hyperpolarization-activated cyclic nucleotide gated (HCN) channel.

13. The bypass tract of claim 12, wherein the HCN channel is HCN2.

* * * * *

UNITED STATES PATENT AND TRADEMARK OFFICE
CERTIFICATE OF CORRECTION

PATENT NO.      : 8,435,509 B2                          Page 1 of 1
APPLICATION NO. : 13/109804
DATED           : May 7, 2013
INVENTOR(S)     : Peter R. Brink et al.

It is certified that error appears in the above-identified patent and that said Letters Patent is hereby corrected as shown below:

> On the title page item (73), in addition to Assignee: The Trustees of Columbia University in the City of New York, New York, NY (US), the patent should also include Assignee: The Research Foundation of State University of New York, Albany, NY (US).

Signed and Sealed this
Third Day of November, 2015

Michelle K. Lee
*Director of the United States Patent and Trademark Office*